United States Patent [19]
VanGemert

[11] Patent Number: 5,274,132
[45] Date of Patent: Dec. 28, 1993

[54] PHOTOCHROMIC NAPHTHOPYRAN COMPOUNDS

[75] Inventor: Barry VanGemert, Murrysville, Pa.

[73] Assignee: Transitions Optical, Inc., Pinellas Park, Fla.

[21] Appl. No.: 954,630

[22] Filed: Sep. 30, 1992

[51] Int. Cl.$^5$ .................... C07D 311/92; C08K 5/15; G02B 27/00

[52] U.S. Cl. .................... 549/389; 549/60; 524/110; 524/109; 524/99; 351/163

[58] Field of Search .................. 549/389, 60; 524/110, 524/109, 99; 351/163

[56] References Cited

U.S. PATENT DOCUMENTS

| | | | |
|---|---|---|---|
| 3,567,605 | 3/1971 | Becker | 204/158 |
| 3,627,690 | 12/1971 | Casella et al. | 549/389 |
| 4,342,668 | 8/1982 | Hovey et al. | 252/586 |
| 4,563,458 | 1/1986 | Widdig et al. | 514/253 |
| 4,637,698 | 1/1987 | Kwak et al. | 351/163 |
| 4,720,356 | 1/1988 | Chu | 252/586 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,931,221 | 6/1990 | Heller et al. | 252/586 |
| 5,066,818 | 11/1991 | Van Gemert | 549/389 |

FOREIGN PATENT DOCUMENTS 294056 12/1988 European Pat. Off. .
2-69471 3/1990 Japan .

OTHER PUBLICATIONS

Padwa et al., J. Org. Chem., vol. 40, No. 8, 1975.
Photochromic Properties of 2-Hydroxychalcones in Solution and Polymers, R. Matsushimi et al., Bull. Chem. Soc., Japan, vol. 65, pp. 39-45 (1992).
Esa T. Jarvi et al., J. Am. Chem. Soc., vol. 204, No. 25, 1982, pp. 7196-7204.

*Primary Examiner*—Nicky Chan
*Attorney, Agent, or Firm*—Irwin M. Stein

[57] ABSTRACT

Described are novel reversible photochromic naphthopyran compounds, examples of which are 3-aryl-3-arylalkenyl naphthopyrans. Also described are organic host materials that contain or that are coated with such compounds. Articles such as ophthalmic lenses or other plastic transparencies that incorporate the novel naphthopyran compounds or combinations thereof with complementary photochromic compounds, e.g., spiro(indoline) type compounds, are also described.

16 Claims, No Drawings

PHOTOCHROMIC NAPHTHOPYRAN COMPOUNDS

DESCRIPTION OF THE INVENTION

The present invention relates to certain novel naphthopyran compounds. More particularly, this invention relates to novel photochromic naphthopyran compounds, and to compositions and articles containing such novel naphthopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about $-30°$ C. Irradiation of the compounds with visible light or upon raising the temperature to above about $0°$ C. is reported to reverse the coloration to a colorless state.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes have been of interest because of the potential safety features that such transparencies offer.

Photochromic compounds useful in optical applications, such as conventional ophthalmic lenses, are those which possess (a) a high quantum efficiency for coloring in the near ultraviolet, (b) a low quantum yield for bleaching with white light and (c) a relatively fast thermal fade at ambient temperature but not so rapid a thermal fade rate that the combination of white light bleaching and thermal fade prevent coloring by the ultraviolet component of strong sunlight. In addition, the aforesaid properties are desirably retained in conventional rigid synthetic plastic materials customarily used for ophthalmic and plano lenses when such materials have applied to or incorporated therein such photochromic compounds.

Compounds, such as 3,3-diphenyl-3H-naphtho[2,1-b]pyran, change color on exposure to the near ultraviolet; but, at room temperature and above, this compound bleaches too rapidly for use in an ophthalmic lens. Substitution of either or both of the phenyl rings at the meta and para positions results in an even more rapid bleach rate, and therefore an even lower color intensity. The compound, 2,2-diphenyl-2H-naphtho[1,2-b]pyran, also colors on exposure to near ultraviolet light at room temperature but does not bleach in a reasonable period of time. Substitution of either or both of the phenyl rings at the meta and para positions have little effect on the rate of bleaching of these compounds.

In accordance with the present invention, it has now been discovered that certain novel naphthopyran compounds having a high quantum efficiency for coloring in the near ultraviolet and an acceptable rate of fade may be prepared. These compounds may be described as 3-aryl-3-arylalkenyl naphthopyrans, and may be represented by the following graphic formula I:

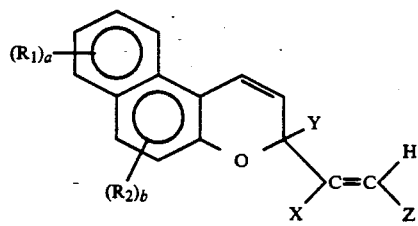

In graphic formula I, X may be selected from the group consisting of hydrogen and $C_1$-$C_4$ alkyl. Preferably X is selected from the group consisting of hydrogen and methyl. Y and Z may each be selected from the group consisting of substituted and unsubstituted naphthyl, furyl, thienyl and phenyl, said substituents being selected from the group consisting of $C_1$-$C_4$ alkyl, $C_1$-$C_4$ alkoxy, chloro and fluoro. Preferably Y and Z are each selected from the group consisting of phenyl and substituted phenyl. $R_1$ and $R_2$ are each selected from the group consisting of $C_1$-$C_5$ acyloxy, benzoyloxy, $C_1$-$C_{10}$ alkyl, $C_5$-$C_7$ cycloalkyl, phenyl, mono- or di-substituted phenyl, $C_1$-$C_4$ alkoxy, halogen, acrylyl, methacrylyl, acryloxy ($C_1$-$C_4$) alkyl, furyl and thienyl, said phenyl substituents being selected from the group consisting of $C_1$-$C_4$ alkyl, $C_1$-$C_4$ alkoxy, chloro and bromo, and "a" and "b" are each integers of from 0 to 2, i.e., 0, 1, or 2, the sum of a and b preferably being not more than 2.

Compounds represented by graphic formula I may be prepared by reaction of the appropriately substituted benzylidene-acetophenones (chalcone) with sodium acetylide in a suitable solvent, such as dry tetrahydrofuran, to obtain the corresponding propargyl alcohol. This propargyl alcohol is then coupled with 2-naphthol under acidic conditions to give the desired naphthopyran. If the starting chalcone is not commercially available, it may be prepared by condensing an appropriately substituted or unsubstituted acyl substituted aromatic (or furan or thiophen) compound, e.g., acetophenone, with an appropriately substituted or unsubstituted aromatic (or furan or thiophen) aldehyde, e.g., benzaldehyde, in accordance with the following equation:

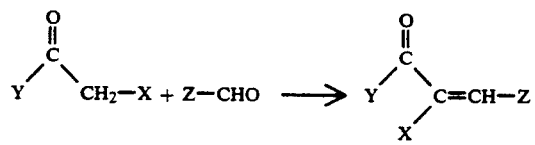

In the above equation, X, Y and Z are the same as described with respect to graphic formula I.

The condensation of aldehydes with substituted acetophenones is described in *Organic Reactions*, Volume 16, A. C. Cope, Editor, John Wiley & Sons, Inc., 1968, New York, "The Aldol Condensation" by A. T. Nielsen and W. J. Houlihan.

Examples of chalcones are listed in Table XVII of that publication beginning at page 280. Of particular interest are the following chalcones:

(1) benzylideneacetophenone
(2) 4'methoxychalcone
(3) 4 methoxychalcone
(4) alpha-methylchalcone
(5) 1-(2-benzoylvinyl)naphthalene
(6) 1-(5-methyl-2-thienyl)-3-phenyl-2-propen-1-one
(7) 1-phenyl-3-(2-thienyl)-2-propen-1-one
(8) 1-phenyl-3-(2-furyl)-2-propen-1-one Compounds represented by graphic formula I may be used in those applications in which organic photochromic substances may be employed, such as optical lenses, e.g., ophthalmic and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans represented by graphic formula I exhibit color changes from colorless to colors ranging from yellow to orange.

Examples of contemplated naphthopyrans are the following:

(1) 3-phenyl-3-(2-phenylvinyl)-3H-naphtho[2,1-b]pyran
(2) 3-methoxyphenyl-3-(2-phenylvinyl)-3H-naphtho[2,1-b]pyran
(3) 3-phenyl-3-(2-(4-methoxyphenyl)vinyl)-3H-naphtho[2,1-b]pyran
(4) 3-phenyl-3-(2-phenyl-1-methylvinyl)-3H-naphtho[2,1-b]pyran
(5) 3-phenyl-3-(2-(1-naphthyl)vinyl)-3H-naphtho[2,1-b]pyran
(6) 3-(5-methyl-2-thienyl)-3-(2-phenylvinyl)-3H-naphtho[2,1-b]pyran
(7) 3-phenyl-3-(2-(2-thienyl)vinyl)-3H-naphtho[2,1-b]pyran.
(8) 3-phenyl-3-(2-(2-furyl)vinyl)-3H-naphtho[2,1-b]pyran The naphthopyran compounds described in the specification and claims may be dissolved in common organic solvents such as benzene, toluene, chloroform, ethyl acetate, methyl ethyl ketone, acetone, ethyl alcohol, methyl alcohol, acetonitrile, tetrahydrofuran, dioxane, methyl ether of ethylene glycol, dimethylformamide, dimethylsulfoxide, methyl Cellosolve, morpholine and ethylene glycol. These naphthopyrans are also soluble in synthetic plastic materials customarily used for plastic optical lenses, both plano and ophthalmic, e.g., materials such as methyl methacrylate, polycarbonates and polymerizates prepared from CR-39 ® diallyl glycol carbonate monomer. They may also be dispersed in fluorocarbons and in liquids containing water and/or alcohols.

The aforedescribed naphthopyran compounds may also be dissolved in colorless or transparent solutions prepared from transparent organic host materials, e.g., transparent polymers (homopolymers or copolymers) or blends of such transparent polymers and optionally a suitable organic solvent, e.g., polymers of transparent organic host materials described hereinafter dissolved in one or more of the aforedescribed organic solvents. Examples of such solutions include a poly(vinyl acetate)-acetone solution, a nitrocellulose-acetonitrile solution, a poly(vinyl chloride)-methyl ethyl ketone solution, a poly(methylmethacrylate)-acetone solution, a cellulose acetate-dimethylformamide solution, a poly(vinyl pyrrolidone)-acetonitrile solution, a polystyrene-benzene solution and an ethyl cellulose-methylene chloride solution.

The aforesaid photochromic solutions or compositions may be applied to a compatible host material, e.g., a transparent support, such as cellulose triacetate, polyethylene terephthalate or baryta paper and dried to obtain an article that will color on exposure to ultraviolet radiation and that will return to its original state by removing the source of ultraviolet radiation. The naphthopyran compounds (or compositions containing them) described in the specification and claims may be applied to or incorporated also within a coating composition applied to a compatible support; or applied to or incorporated within the article comprising the compatible host, e.g., a polymerized organic material such as a synthetic polymeric plastic host material.

On irradiation of the compounds of graphic formula I with ultraviolet light, the naphthopyran ring opens reversibly at the carbon-oxygen bond between the number 3-carbon atom and the ring oxygen. The formation of the open form of the colorless compound is believed to be responsible for the coloring observed on exposure to ultraviolet light. It is also believed that the extension of the chromophore by the double bond may be responsible for the bathochromic shift relative to the benzopyrans and naphthopyrans disclosed in U.S. Pat. No. 3,567,605. The colored form of the photochromic compounds of graphic formula I will fade to the colorless state at normal ambient temperatures when not exposed to ultraviolet light.

Commercially available photoreactive inorganic glass lenses containing silver halide particles darken to a gray or brown color in sunlight. In order to duplicate this color change in a plastic lens using the organic photochromic naphthopyrans of graphic formula I, it is contemplated that such naphthopyrans be used in combination with other appropriate complementary organic photochromic materials so that together they produce the desired gray or brown color shade when the plastic lens containing such photochromic materials is exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue coloring compound. Particularly contemplated classes of other complementary organic photochromic compounds that may be used include: spiro(indoline)-type compounds such as spiro(indoline)naphthoxazines, spiro(benzindoline)naphthoxazines, spiro(benzindoline)naphthopyrans, spiro(indoline)benzopyrans, spiro(benzindoline)benzoxazines, chromenes, e.g., benzopyrans and other naphthopyrans, metal dithizonate compounds, fulgides or fulgimides and spiro(di)hydroindolizines.

The photochromic naphthopyran compounds of graphic formula I may also be used alone or in combination with other photochromic compounds in applications other than photochromic optical lenses. For example, they may be applied and/or incorporated within novelty items such as toys, wearing apparel and posters and items such as security documents requiring verification of authenticity.

More particularly, spiro(indoline)pyrido benzoxazine photochromic compounds described in U.S. Pat. Nos. 4,637,698 and 5,066,818 and spiro(indoline)naphthoxazines described in U.S. Pat. Nos. 3,562,172, 3,578,602, 4,215,010 and 4,342,668 are reported to color to blue when activated. See the disclosure of U.S. Pat. No. 5,066,818 from column 6, line 30 to column 13, line 34 for examples of the aforesaid spiro(indoline) type compounds. These compounds may be used in admixture with or in conjunction with the yellow-orange novel naphthopyran photochromic compounds described in this application.

The naphthopyran compounds of the present invention may be combined with other complementary organic photochromic compounds, as herein described, such as spiro(indoline)pyrido benzoxazine or spiro(indoline)naphthoxazine compounds in amounts and in a ratio such that an organic host material to which the mixture of compounds is applied or in which they are incorporated exhibits a substantially neutral color when activated with unfiltered sunlight, i.e., as near a neutral color as possible given the colors of the activated naphthopyran and spiro-oxazine photochromic compounds. The relative amounts of the oxazine and pyran compounds used will vary and depend in part upon the relative intensities of the color of the activated species of such compounds. Similarly, the naphthopyran compounds of the present invention may be combined with spiro(indoline)benzoxazine compounds, as described in U.S. Pat. No. 4,816,584, in amounts and in a ratio such that an organic host material to which the mixture of compounds is applied or in which they are incorporated exhibits a near-brown color. Generally, the weight ratio of the aforedescribed spiro(indoline)oxazine compound(s) to the naphthopyran compound(s) of the present invention will vary from about 1:3 to about 3:1, e.g., between about 1:2 or 0.75:1 and about 2:1.

Photochromic compounds of the present invention, mixtures of such compounds with other photochromic compounds, or compositions containing same (hereinafter "photochromic substances") may be applied to or incorporated into a host material by various methods described in the art. Such methods include dissolving or dispersing the substance within the host material, e.g., imbibition of the photochromic substance into the host material by immersion of the host material in a hot solution of the photochromic substance or by thermal transfer; providing the photochromic substance as a separate layer between adjacent layers of the host material, e.g., as a part of a polymer film; and applying the photochromic substance as part of a coating placed on the surface of the host material. The term "imbibition" or "imbibe" is intended to mean and include permeation of the photochromic substance alone into the host material, solvent assisted transfer absorption of the photochromic substance into a porous polymer, vapor phase transfer, and other such transfer mechanisms. See U.S. Pat. No. 5,066,818 column 14, line 41 to column 15, line 25 for examples of the above methods.

In addition, imbibition of photochromic substances into a host material may be accomplished by the method described in U.K. Patent Application 2,174,711. In that method a substantially mottle-free, substantially homogeneous film of polymeric resin having the photochromic substance dissolved therein is applied to the surface of the host material. The film-bearing host material is heated to temperatures near to but below the melting temperature of the photochromic substance for a time sufficient to incorporate a photochromic amount of the photochromic substance into the surface of the host. The photochromic-depleted film is then removed from the host surface with a suitable solvent.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

Typically, tinting is accomplished by immersion of the host material in a heated aqueous dispersion of the selected dye. The degree of tint is controlled by the temperature of the dye bath and the length of time the host material is allowed to remain in the bath. Generally, the dye bath is at temperatures of less than 100° C., e.g., from 70° C. to 90° C., such as 80° C., and the host material remains in the bath for less than five (5) minutes, e.g., between about 0.5 and 3 minutes, e.g., about 2 minutes. The degree of tint is such that the resulting article exhibits from about 70 to 85 percent, e.g., 80–82 percent, light transmission.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings and/or coatings that serve as oxygen barriers. Such coatings are known in the art.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should not be such that it masks the color of the activated form of the photochromic substance, i.e., so the change in color is readily apparent to the observer. Preferably, the host material article is a solid transparent or optically clear material.

Examples of host materials which may be used with the photochromic substances or compositions described herein include: polymers, i.e., homopolymers and copolymers, of polyol(allyl carbonate) monomers, e.g., diethylene glycol bis(allyl carbonate), polymers, i.e., homopolymers and copolymers, of polyfunctional acrylate monomers, polyacrylates, poly(alkylacrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, poly(ethylene terephthalate), polystyrene, copoly(styrene-methyl methacrylate) copoly(styrene-acrylonitrile), polyvinylbutyral and polymers, i.e., homopolymers and copolymers, of diallylidene pentaerythritol, particularly copolymers with polyol (ally carbonate) monomers, e.g., diethylene glycol bis(allyl carbonate), and acrylate monomers.

Transparent copolymers and blends of the transparent polymers are also suitable as host materials. Preferably, the host material is an optically clear polymerized organic material prepared from a polycarbonate resin, such as the carbonate-linked resin derived from bisphenol A and phosgene, i.e., poly(4,4'-dioxydiphenol-2,2-propane), which is sold under the trademark, LEXAN; a poly(methyl methacrylate), such as the material sold under the trademark, PLEXIGLAS; polymerizates of a polyol(allyl carbonate), especially diethylene glycol bis(allyl carbonate), which monomer is sold under the trademark, CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80-90 percent diethylene glycol bis(allyl carbonate) and 10-20 percent vinyl acetate, particularly 80-85 percent of the bis(allyl carbonate) and 15-20 percent vinyl acetate, and copolymers with a polyurethane having terminal diacrylate functionality, as described in U.S. Pat. No. 4,360,653, cellulose acetate, cellulose propionate, cellulose butyrate, cellulose acetate butyrate, polystyrene and copolymers of styrene with methyl methacrylate, vinyl acetate and acrylonitrile.

Polyol (allyl carbonate) monomers which may be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g., glycols. The monomers can be prepared by procedures well known in the art, e.g., U.S. Pat. Nos. 2,370,567 and 2,403,113.

The amount of photochromic substance or composition-containing same applied to or incorporated into a host material is not critical provided that a sufficient amount is used to produce a photochromic effect discernible to the naked eye. Generally such amount can be described as a photochromic amount. The particular amount used depends often upon the intensity of color desired upon irradiation thereof and upon the method used to incorporate or apply the photochromic substances. Typically, the more compound applied or incorporated, the greater is the color intensity. Generally, the amount of each photochromic substance incorporated into or applied to the host material may range from about 0.01 or 0.05 to about 10 to 20 percent by weight. More typically, the amount of photochromic substance(s) incorporated into or applied to the host material will range from about 0.01 to about 2 weight percent, more particularly, from about 0.01 to about 1 weight percent, e.g., from about 0.1 or 0.5 to about 1 weight percent, based on the weight of the host material. Expressed differently, the total amount of photochromic substance incorporated into or applied to an optical host material may range from about 0.15 to about 0.35 milligrams per square centimeter of surface to which the photochromic substance(s) is incorporated or applied.

The present invention is more particularly described in the following examples which are intended as illustrative only, since numerous modifications and variations therein will be apparent to those skilled in the art.

EXAMPLE 1

Step 1

Five grams of sodium hydroxide were dissolved in a mixture of 50 milliliters of water and 40 milliliters of ethanol. Acetophenone (0.1 mole, 12.0 grams) and p-anisaldehyde (0.1 mole, 13.6 grams) were added to the stirred solution at room temperature. After stirring about one and a half hours, the resultant solid product, 4-methoxychalcone (approximately 23 grams), was suction filtered and dried.

Step 2

4-methoxychalcone (10 grams) from Step 1 was dissolved in 150 milliliters (ml) of tetrahydrofuran saturated with acetylene and stirred at room temperature under nitrogen. 20 grams of an 18 weight percent suspension of sodium acetylide in xylene/light mineral oil (a product purchased from Farchan Chemical) were added in one portion to the solution and stirring continued. Liquid chromatography analysis indicated two products forming, i.e., the desired propargyl alcohol and a small amount of tetra substituted butyne diol. After fifteen hours, the mixture was poured into 100 ml of cold water. The organic layer was separated and washed once with water. The aqueous fractions were back extracted with ether and the organic portions were combined. The solvents were removed on a rotary evaporator to yield an oil-like material containing the product, 1-(4-methoxyphenyl)-3-phenyl-1-penten-4-yn-3-ol.

STEP 3

Approximately one-half, based on volume, of the oil product from Step 2 and 5 grams of 2-naphthol were dissolved in 150 milliliters of toluene and stirred. Dodecylbenzene sulfonic acid was added drop-wise until a deep orange color was obtained. The mixture was stirred at room temperature for two hours and then poured into water. The organic layer was washed twice with water then once with 10 weight percent aqueous sodium hydroxide and finally with water again. The toluene solvent was removed on a rotary evaporator and the residue chromatographed on silica using a hexane:chloroform (1:1) mixture as the elutant. The photochromic fractions were combined and the solvents removed on a rotary evaporator. The residue was induced to crystallize by dissolving it in hexane:diethyl ether (approximately 2:1 ratio). The crystals (1.4 grams) were suction filtered and washed with hexane. The crystalline product melted at 126°-128° C. and was 92% pure by liquid chromatographic analysis. A nuclear magnetic resonance (NMR) spectrum showed the solid crystalline product to be 3-phenyl-3-(2-(4-methoxyphenyl)-vinyl)-3H-naphtho[2,1-b]pyran.

EXAMPLE 2

The procedure of Step 1 of Example 1 was followed except that 1-naphthaldehyde (0.1 mole, 15.6 grams) was substituted for p-anisaldehyde. After stirring for 2 hours, the mixture was poured into water and extracted into methylene chloride. The solvent was removed by evaporation to yield the oil 1-(2-benzoylvinyl)naphthalene that later crystallized. The procedure of Step 2 of Example 1 was followed using 1-(2-benzoylvinyl)naphthalene in place of 4 methoxychalcone of Example 1. The product was an oil containing 1-(1-naphthyl)-3-phenyl-1-penten-4-yn-3-ol which was used without purification in the next step.

The procedure of Step 3 of Example 1 was used with the following exceptions: all of the product from Step 2 was used, the mixture was stirred for 15 hours, the product was chromatographed on silica using a hexane:-chloroform (2:1) eluant, and the product was crystallized using hexane. The crystals (0.9 grams) melted at 109°-110° C., were 98% pure by liquid chromatographic analysis, and had a NMR spectrum that was consistent with the product, 3-phenyl-3-(2-(1-naphthyl)-vinyl)-3H-naphtho[2,1-b]pyran.

EXAMPLE 3

Benzaldehyde (0.1 mole, 10.6 grams) and propiophenone (0.1 mole, 13.4 grams) were added to 100 milliliters of ethanol containing a few milliliters of a 10 weight percent aqueous sodium hydroxide solution. The mixture was heated to 50° C. for four hours at which point liquid chromatographic analysis indicated the reaction to be substantially complete. Most of the ethanol was removed on a rotary evaporator followed by the addition of water and methylene chloride. The organic phase was separated, washed with water again and solvent removed on a rotary evaporator. The residual oil was vacuum distilled, ten grams being collected at a boiling point range of 220°-230° C. at 25 mm pressure. The NMR spectrum of this material confirmed it to be the desired alpha methylchalcone.

The procedure of Step 2 of Example 1 was followed except that alpha methylchalcone (10 grams) was substituted for 4-methoxy chalcone and the mixture was stirred for 3 hours instead of 15 hours. The product was an oil containing 1,3-diphenyl-2-methyl-1-penten-4-yn-3-ol which was used directly in the next step.

The procedure of Step 3 of Example 1 was followed except for the following: 200 milliliters of toluene was used, the mixture was stirred for 15 hours, and chromatographed using a hexane:chloroform ratio of 2:1. The recovered crystalline product (1.5 grams) melted at 131°-132° C., was 99% pure as determined by liquid chromatographic analysis, and had a NMR spectrum that was consistent with the product, 3-phenyl-3-(2-phenyl-1-methylvinyl)-3H-naphtho[2,1-b]pyran.

EXAMPLE 4

The procedure of Step 2 of Example 1 was followed except that 4'-methoxychalcone (10 grams) was used and the mixture was stirred 4 hours. The product was an oil containing 1-phenyl-3-(4-methoxyphenyl)-1-penten-4-yn-3-ol, which was used directly in the next step.

The procedure of Step 3 of Example 1 was followed except that 200 milliliters of toluene was used and the mixture was stirred for 6 hours. The resulting residue was induced to crystallize by dissolving it in a small amount of hexane and allowing the solution to stand overnight. The crystalline product (2.9 grams) melted at 101°-103° C., was 98% pure by liquid chromatographic analysis, and had a NMR spectrum that was consistent with the product, 3-methoxyphenyl-3-(2-phenylvinyl)-3H-naphtho[2,1-b]pyran.

EXAMPLE 5

Benzylidene-acetophenone (10 grams) was dissolved in 150 milliliters of tetrahydrofuran and stirred at room temperature under nitrogen. 15 milliliters of an 18 weight percent solution of sodium acetylide in xylene/light mineral oil was added in one portion and stirring continued. After four hours, the mixture was poured into 100 milliliters of cold water. The organic layer was separated and washed once with water. The aqueous fractions were back extracted with ether and the organic portions were combined. The solvents were removed on a rotary evaporator to give an oil-like product containing 1,3-diphenyl-1-penten-4-yn-3-ol. This oil was used directly in the next step.

The product from the previous reaction was dissolved in 150 milliliters of toluene along with 10 grams of 2-naphthol and 30 grams of acidic alumina. The mixture was heated with stirring to 100° C. and held there for three hours. The mixture was cooled and then filtered to remove the alumina. The alumina was extracted with two 50 milliliters portions of ethyl acetate, the organic portions were combined and solvents removed on a rotary evaporator. The residue was chromatographed on silica using hexane:chloroform (4:1) as elutant. The photochromic fractions were combined and the solvent removed on a rotary evaporator. The residue was induced to crystallize by cooling the oil dissolved in a hexane:diethylether mixture. The recovered crystalline product (1.0 g) melted at 137°-138° C., was 96% pure as determined by liquid chromatographic analysis, and had a NMR spectrum that was consistent with the product 3-phenyl-3-(2-phenylvinyl)-3H-naphtho[2,1-b]pyran.

COMPARATIVE EXAMPLE 1

To a 500 milliliter reaction flask were added 0.1 mole of 1,1-diphenyl-2-propyn-1-ol (20.8 grams), 2-naphthol (515 grams) and 200 milliliters of benzene. The reaction mixture was warmed to 55° C. to dissolve all of the naphthol reactant. After all of the 2-naphthol was dissolved, 0.25 grams of p-toluene sulfonic acid was added to the stirred reaction mixture, which then changed from light tan to dark black and exothermed to 70° C. A few minutes later, the reaction mixture lightened and began to cool. After 30 minutes, the reaction mixture was poured into 100 milliliters of 10 percent aqueous sodium hydroxide and shaken. The organic phase was washed once with 10 percent aqueous sodium hydroxide and then washed with water. The benzene solvent was removed on a rotary evaporator. The resulting solid residue was a light tan solid, which was slurried with 100 milliliters of hexane and then filtered. The filtered solid was washed again with 100 milliliters of hexane and dried to provide 18.4 grams of the product, 3,3-diphenyl-3H-naphtho[2,1-b]pyran, which was found to be 98 percent pure by liquid chromatographic analysis. The product had a melting point range of 156°-158° C.

COMPARATIVE EXAMPLE 2

Anisole (0.1 mole, 10.8 grams) and benzoyl chloride (0.1 mole, 14 grams) were dissolved in 200 milliliters of hexane and stirred at room temperature while 15 grams of anhydrous aluminum chloride were added slowly over a period of 15 minutes. The reaction mixture was stirred an additional 15 minutes and then the hexane decanted. The resulting viscous residue in the reaction flask was carefully hydrolyzed with 200 milliliters of a mixture of ice and dilute hydrochloric acid. The resulting organic fraction was taken up in dichloromethane and the resulting solution washed with water. Dichloromethane solvent was removed on a rotary evaporator leaving an oil product that solidified on standing. The solidified product was broken-up, washed with two 50 milliliters portions of pentane, and suction dried yielding 4-methoxybenzophenone.

10 grams of this 4-methoxybenzophenone was converted to the propargyl alcohol by the procedure described in Example 1, Step 2. NMR analysis of the resulting product showed it to be a mixture of 1-phenyl-1(4-methoxyphenyl)-2-propyn-1-ol and the starting ketone, 4-methoxybenzophenone, in a ratio of 3:1.

The crude propargyl alcohol from the previous step was added to a slurry of 2-naphthol (5 grams), anhydrous acid alumina (40 grams) and 200 milliliters of toluene. The resulting reaction mixture was heated to reflux for 30 minutes, cooled and filtered. The alumina was washed two times with 100 milliliter portions of hexane. The toluene and hexane fractions were combined and the organic solvents removed on a rotary evaporator. The resulting product was an orange oil that crystallized from a mixture of hexane and diethyl ether. The product crystals were washed with diethyl ether and dried to give 1.4 grams of a product having a melting range of 149°-150° C. NMR analysis confirmed the product to be 3-phenyl-3(4-methoxyphenyl)-3H-naphtho[2,1-b]pyran.

Selected naphthopyrans prepared in the above-described Examples were incorporated into test samples of an ethyl cellulose resin by the following procedure. 25 milligrams of the selected photochromic compound was added to 2.0 grams of a 10 weight percent ethyl cellulose solution in toluene. The compounds were dissolved by warming and stirring on a steam bath. Approximately 2.0 grams of each solution was deposited on the edge of a 75 by 25 millimeter (mm) glass slide. Using a draw down bar, an 8 mm layer of photochromic resin solution was evenly placed on the slide. After the resin layer dried, the samples were tested on an optical bench to determine if comparable UV absorbance levels at 347 nm were obtained. If the absorbance levels differed by more than 10 percent, the amount of naphthopyran was adjusted accordingly.

Further testing was done on selected naphthopyrans that were imbibed by thermal transfer into test squares of a homopolymer of diethylene glycol bis(allyl carbonate) by the following procedure. Each naphthopyran was dissolved into toluene solvent to form a 4 weight percent solution of the compound. A piece of No. 4 Whatman filter paper was saturated with the naphthopyran solution and allowed to air dry. The dried filter paper was placed on one side of the polymer test square, which measured ⅛ inch (0.3 centimeter)×2 inch (5.1 centimeters)×2 inch (5.1 centimeters). A piece of untreated filter paper was placed on the other side of the polymer test square and the resulting sandwich placed between two plates of flat aluminum metal plates. The entire assembly was then placed in a 155° C. oven for a time sufficient to thermally transfer the naphthopyran into the polymer test square. Residence times in the oven were adjusted to imbibe comparable amounts of the naphthopyran compounds in order to yield a comparable UV absorbance at 347 nm. The imbibed test squares were washed with acetone after removal from the oven.

Both sets of polymer test samples were tested for photochromic response rates on an optical bench. The samples were illuminated by a 150 watt Xenon lamp fitted with a copper sulfate bath and a neutral density filter at an intensity of about one sun. A second beam of light provided by a filtered tungsten lamp arranged to pass through the sample area exposed by the UV source was used to monitor changes in transmission of the sample over different wavelength ranges in the visible region of the spectrum. The intensity of the monitoring beam after passing through the sample was measured by means of an IL-1500 radiometer equipped with a silicon detector head and matching filters.

The $\Delta$ OD/Min, which represents the sensitivity of the photochromic compound's response to UV light, was measured using photopic filters on the silicon detector. The response of the filtered detector approximated the luminosity curve. The $\Delta$ OD was measured over the first five (5) seconds of UV exposure, then expressed on a per minute basis. The saturation optical density (OD) was taken under identical conditions as the $\Delta$ OD/Min, except UV exposure was continued for 15 minutes for the examples in Table 1 and for 20 minutes for the examples in Table 2. The lambda max reported in Tables 1 and 2 is the wavelength in the visible spectrum at which the maximum absorption of the activated (colored) form of the photochromic compound in ethyl cellulose resin in Table 1 and in poly (diethylene glycol bis (allyl carbonate)) in Table 2 occurs. The Bleach Rate T ½ (SEC.) is the time interval in seconds for the absorbance of the activated form of the naphthopyran in the test polymers to reach one half the highest absorbance at room temperature (72° F., 22.2° C.) after removal of the source of activating light. Results are tabulated in Tables 1 and 2.

TABLE 1

|  | LAMBDA MAX | $\Delta$ OD/Min SENSITIVITY | $\Delta$ OD @ SATURATION | BLEACH T ½ (SEC.) |
|---|---|---|---|---|
| COMPOUND EXAMPLE | | | | |
| 1 | 492 nm | 0.93 | 0.85 | 224 |
| 2 | 480 nm | 1.02 | 0.84 | 309 |
| 3 | 447 nm | 1.08 | 0.60 | 75 |
| 4 | 467 nm | 0.86 | 0.54 | 128 |
| COMPARATIVE EXAMPLE | | | | |

TABLE 1-continued

| | LAMBDA MAX | Δ OD/Min SENSITIVITY | Δ OD @ SATURATION | BLEACH T ½ (SEC.) |
|---|---|---|---|---|
| 1 | 432 nm | 0.87 | 0.31 | 32 |

TABLE 2

| | LAMBDA MAX | Δ OD/Min SENSITIVITY | Δ A OD @ SATURATION | BLEACH T ½ (SEC.) |
|---|---|---|---|---|
| COMPOUND EXAMPLE | | | | |
| 5 | 470 nm | 0.89 | 0.70 | 182 |
| COMPARATIVE EXAMPLE | | | | |
| 1 | 432 nm | 0.87 | 0.36 | 45 |
| 2 | 468 nm | 0.66 | 0.25 | 35 |
| a. | 476 nm | 0.45 | 1.36 | >30 min | a. Purchased 2,2-diphenyl-2H-naphthol[1,2-b]pyran

The results for Compound Examples 1 through 5 that are listed in Tables 1 and 2 demonstrate the effects on the tested parameters of various substituents at the X, Y and Z positions on graphic formula 1. The Compound Example with particularly useful properties for optical application is Compound Example 2 which has hydrogen as X, phenyl as Y, and 2-naphthyl as Z. The Comparative Examples have unacceptable bleach rates which are either too fast (Comparative Examples 1 and 2) or too slow (Comparative Example a.).

Although the present invention has been described with reference to the specific details of particular embodiments thereof, it is not intended that such details be regarded upon the scope of the invention except insofar as to the extent that they are included in the accompanying claims.

I claim:

1. A naphthopyran compound represented by the following graphic formula:

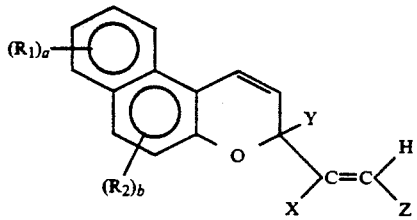

wherein $R_1$ and $R_2$ are each selected from the group consisting of $C_1$-$C_5$ acyloxy, benzoyloxy, $C_1$-$C_{10}$ alkyl, $C_5$-$C_7$ cycloalkyl, phenyl, mono- or di-substituted phenyl, $C_1$-$C_4$ alkoxy, halogen, acrylyl, methacrylyl, acryloxy ($C_1$-$C_4$) alkyl, methacryloxy ($C_1$-$C_4$) alkyl, furyl and thienyl, said phenyl substituents being selected from the group consisting of $C_1$-$C_4$ alkyl, $C_1$-$C_4$ alkoxy, chloro and bromo, a and b are each integers of from 0 to 2, X is selected from the group consisting of hydrogen and $C_1$-$C_4$ alkyl, and Y and Z are each selected from the group consisting of substituted and unsubstituted naphthyl, furyl, thienyl and phenyl, said substituents being selected from the group consisting of $C_1$-$C_4$ alkyl $C_1$-$C_4$ alkoxy, chloro and fluoro.

2. A naphthopyran compound according to claim 1, wherein $R_1$ and $R_2$ are each selected from the group consisting of $C_1$-$C_3$ alkyl, $C_1$-$C_3$ alkoxy, chloro, bromo, phenyl and $C_1$-$C_3$ alkoxyphenyl, X is selected from the group consisting of hydrogen and methyl, and Y and Z are each selected from the group consisting of phenyl and substituted phenyl.

3. A naphthopyran compound according to claim 2, wherein the phenyl substituents are selected from the group consisting of $C_1$-$C_2$ alkyl, $C_1$-$C_2$ alkoxy, and fluoro.

4. A photochromic article comprising a polymerized organic host material and a photochromic amount of a naphthopyran compound represented by the following graphic formula:

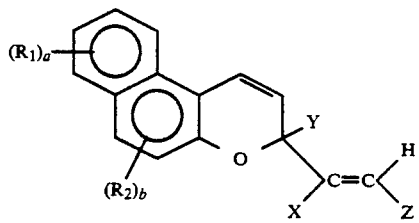

wherein $R_1$ and $R_2$ are each selected from the group consisting of $C_1$-$C_5$ acyloxy, benzoyloxy, $C_1$-$C_{10}$ alkyl, $C_5$-$C_7$ cycloalkyl, phenyl, mono- or di-substituted phenyl, $C_1$-$C_4$ alkoxy, halogen, acrylyl, methacrylyl, acryloxy ($C_1$-$C_4$) alkyl, methacryloxy ($C_1$-$C_4$) alkyl, furyl and thienyl, said phenyl substituents being selected from the group consisting of $C_1$-$C_4$ alkyl, $C_1$-$C_4$ alkoxy, chloro and bromo, a and b are each integers of from 0 to 2, X is selected from the group consisting of hydrogen and $C_1$-$C_4$ alkyl, and Y and Z are each selected from the group consisting of substituted and unsubstituted naphthyl, furyl, thienyl and phenyl, said substituents being selected from the group consisting of $C_1$-$C_4$ alkyl, $C_1$-$C_4$ alkoxy, chloro and fluoro.

5. The photochromic article of claim 4 wherein the organic host material is selected from the group consisting of polymers of polyol(allyl carbonate) monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methyl-methacrylate), copoly(styrene-acrylonitrile), polyvinylbutyral, and polymers of diallylidene pentaerythritol.

6. The photochromic article of claim 5 wherein X is selected from the group consisting of hydrogen and methyl, Y and Z are each selected from the group consisting of phenyl and substituted phenyl, said phenyl substituents being selected from the group consisting of $C_1$-$C_2$ alkyl, $C_1$-$C_2$ alkoxy and fluoro, and $R_1$ and $R_2$ are each selected from the group consisting of $C_1$-$C_3$ alkyl, $C_1$-$C_3$ alkoxy, chloro, bromo, phenyl and $C_1$-$C_3$ alkoxyphenyl.

7. The photochromic article of claim 6 wherein the organic host material is a solid transparent homopolymer or copolymer of diethylene glycol bis(allyl carbonate), poly(4,4'dioxydiphenol-2,2-propane), poly(methylmethacrylate), or polyvinylbutyral.

8. The photochromic article of claim 7 wherein the photochromic compound is present in an amount of from about 0.01 to 20 weight percent.

9. The photochromic article of claim 7 wherein the article is a lens.

10. A photochromic article comprising a solid transparent polymerized organic host material and a photochromic amount of each of (a) a first photochromic substance selected from the group consisting of spiro(indoline)naphthoxazines, spiro(indoline)pyrido benzoxazines, and spiro(indoline)benzoxazines, and (b) a naphthopyran compound represented by the following graphic formula:

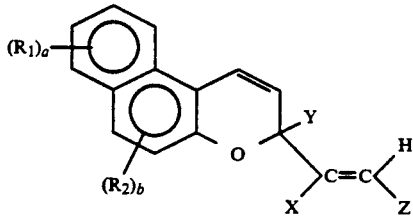

wherein $R_1$ and $R_2$ are each selected from the group consisting of $C_1$-$C_5$ acyloxy, benzoyloxy, $C_1$-$C_{10}$ alkyl, $C_5$-$C_7$ cycloalkyl, phenyl, mono- or di-substituted phenyl, $C_1$-$C_4$ alkoxy, halogen, acrylyl, methacrylyl, acryloxy ($C_1$-$C_4$) alkyl, methacryloxy ($C_1$-$C_4$) alkyl, furyl and thienyl, said phenyl substituents being selected from the group consisting of $C_1$-$C_4$ alkyl, $C_1$-$C_4$ alkoxy, chloro and bromo, a and b are each integers of from 0 to 2, the sum of a and b being not more than 2, X is selected from the group consisting of hydrogen and $C_1$-$C_4$ alkyl, and Y and Z are each selected from the group consisting of substituted and unsubstituted naphthyl, furyl, thienyl and phenyl, said substituents being selected from the group consisting of $C_1$-$C_4$ alkyl, $C_1$-$C_4$ alkoxy, chloro and fluoro.

11. The photochromic article of claim 10 wherein the organic host material is selected from the group consisting of polymers of polyol(allyl carbonate) monomer, polyacrylates, poly(allylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and polymers of diallylidene pentaerythritol.

12. The photochromic article of claim 11 wherein X is selected from the group consisting of hydrogen and methyl, Y and Z are each selected from the group consisting of phenyl, and substituted phenyl, said phenyl substituents being selected from the group consisting of $C_1$-$C_2$ alkyl, $C_1$-$C_2$ alkoxy, and fluoro, and $R_1$ and $R_2$ are each selected from the group consisting of $C_1$-$C_3$ alkyl, $C_1$-$C_3$ alkoxy, chloro, bromo, phenyl and $C_1$-$C_3$ alkoxyphenyl.

13. The photochromic article of claim 12 wherein the organic host material is a solid transparent homopolymer or copolymer of diethylene glycol bis(allyl carbonate), poly(4,4'dioxydiphenol-2,2-propane), poly(methylmethacrylate), or polyvinylbutyral.

14. The photochromic article of claim 13 wherein the total amount of said first photochromic substance and said photochromic naphthopyran compound present in said host material is an amount of from about 0.05 to 10 weight percent.

15. The photochromic articles of claim 14 wherein the weight ratio of the first photochromic substance to the naphthopyran compound is from about 1:3 to about 3:1.

16. The photochromic article of claim 15 wherein the article is an ophthalmic lens.

* * * * *